United States Patent
Tsukuda

(10) Patent No.: US 7,576,855 B2
(45) Date of Patent: Aug. 18, 2009

(54) SPECTROPHOTOMETRIC METHOD AND APPARATUS

(75) Inventor: Yasuo Tsukuda, Kyoto (JP)

(73) Assignee: Shimadzu Corporation, Kyoto-Fu (JP)

( * ) Notice: Subject to any disclaimer, the term of this patent is extended or adjusted under 35 U.S.C. 154(b) by 51 days.

(21) Appl. No.: 11/435,860

(22) Filed: May 18, 2006

(65) Prior Publication Data

US 2006/0263872 A1    Nov. 23, 2006

(30) Foreign Application Priority Data

May 19, 2005    (JP)    ............................. 2005-146934

(51) Int. Cl.
G01J 3/28    (2006.01)

(52) U.S. Cl. ................................... 356/326

(58) Field of Classification Search ................ 356/326, 356/244, 246, 445, 320, 432–444
See application file for complete search history.

(56) References Cited

U.S. PATENT DOCUMENTS

| | | | | |
|---|---|---|---|---|
| 4,682,890 A | * | 7/1987 | de Macario et al. | ......... 356/244 |
| 5,115,133 A | * | 5/1992 | Knudson | ............... 250/339.03 |
| 7,316,899 B2 | * | 1/2008 | McDevitt et al. | ............... 435/6 |
| 2002/0149775 A1 | * | 10/2002 | Mori et al. | ................... 356/445 |

FOREIGN PATENT DOCUMENTS

JP    05-302893 A    11/1993

OTHER PUBLICATIONS

NanoDrop products: NanoDrop 1000 Overview, *Thermo Fischer Scientific*, © 2008, URL: http://www.nanodrop.com/nd-1000-overview.html.

* cited by examiner

*Primary Examiner*—Gregory J Toatley, Jr.
*Assistant Examiner*—Abdullahi Nur
(74) *Attorney, Agent, or Firm*—Sughrue Mion, PLLC

(57) ABSTRACT

Disclosed is a spectrophotometry for a spectral transmission measurement of an extremely small volume of sample solution. A sampler 15 is formed of a flat plate member formed with a sample-holding hole 152 which penetrates the flat plate member in its thickness direction and has a reverse truncated cone shape, and a target sample solution is dropped into the sample-holding hole 152 of the sampler 15 positioned approximately horizontally and held in the hole 152 based on a surface tension of the sample solution in the form of a droplet S. Then, a measurement light is emitted to the held droplet S from directly above. A transmitted light getting out of the droplet S downward is introduced to a diffraction grating 19 through a window plate 17 and a slit 18, and dispersed in a wavelength dependent manner. The resulting light with dispersed wavelength components is detected by a multichannel detector 20 approximately simultaneously.

15 Claims, 5 Drawing Sheets measuring light

SPECTROPHOTOMETRIC METHOD AND APPARATUS

BACKGROUND OF THE INVENTION

1. Field of the Invention

The present invention relates to a spectrophotometric method of irradiating a sample solution with light to measure a transmitted light therefrom, and a spectrophotometric apparatus for use in the spectrophotometric method. More specifically, the present invention relates to a spectrophotometric method and apparatus suitable for spectrophotometrically measuring a small volume of sample solution.

2. Description of the Background Art

In a process for measuring a transmittance or absorbance of a sample solution using a spectrophotometer, such as an ultraviolet-visible spectrophotometer, a rectangular or cylindrical cuvette cell is generally used for containing the sample solution. A typical cuvette cell has an inner volume of several mL or more, and it is required to prepare a sample solution in a sufficient volume to fill the cuvette cell.

Recent years, an ultraviolet-visible spectrophotometer has been increasingly used in the field of biochemistry. In this field, it is often the case that a sample solution for analysis is very small in volume. Particularly, in analyses of DNA, some analyses have to be conducted using only several μL or less of sample solution, due to scarcity and costliness of a sample. Heretofore, there has been known a vessel suitable for spectrophotometrically measuring such a small volume of sample solution [see, for example, Japanese Patent Laid-Open Publication No. 05-302893 [Patent Publication 1)], because the above cuvette cell cannot be used for the purpose of analyzing a small volume of sample solution.

As a cell for use in measuring a small volume of sample solution, a capillary cell has been commonly known that is designed to suck up and hold a sample solution based on a capillary phenomenon. Generally, the capillary cell still requires preparing several μL or more of sample solution at minimum, and cannot be used for any analysis of a sample solution with a volume of less than the lower limit. The capillary cell has another problem about the needs for filling the cell with a sample solution in a complicated manner and taking a lot of time and effort in cleaning after measurement.

As a device allowing for spectrophotometry of a sample solution with an extremely small volume of about 1 μL, there has been known a spectrophotometer ND-100 available from NanoDrop Technologies Inc., USA [see "NanoDrop ND-1000 Overview", NanoDrop Technologies Inc., URL: http://www.nanodrop.com/nd-1000-overview.html (Non-Patent Publication 1)]. As shown in FIG. 9, this spectrophotometer has an upper pedestal 50 and an lower pedestal 52 disposed in vertically opposed relation to one another with a given distance therebetween, and a sample solution 54 is held in a space between the upper and lower pedestals 50, 52 based on a surface tension in a vertically bridging manner. Then, a measurement light is emitted from a light-emitting optical fiber 51 incorporated in the upper pedestal 50 to pass through the sample solution 54, and a transmitted light is received by a light-receiving optical fiber 53 incorporated in the lower pedestal 53. A light path length in the sample solution is set at about 1 mm. It is described that this spectrophotometer is usable in analyses of a sample solution with an extremely small volume of about 1 to 2 μL.

This spectrophotometer involves a time-consuming operation for cleaning respective end faces of the light-emitting and light-receiving optical fibers after completion of a measurement of one sample to perform a measurement of another sample (the Non-Patent Publication 1 describes as "wipe using a laboratory wipe"). While it is desirable to clean the end faces using water or organic solvent because the wiping operation using a laboratory wipe is not sufficient to completely eliminate an influence of a previously-measured sample solution, such a cleaning operation is fairly bothersome. Moreover, this operation has to be performed for each sample measurement, or it is impossible to measure a number of samples while automatically replacing one with another. This analytic operation cannot be the to be efficient. Furthermore, the device designed to partly have a direct contact with a sample solution is likely to cause damages and contamination in the contact portions, and, in that event, an analytic performance will be deteriorated. As measures for avoiding such problems, a lot of times and efforts have to be spent for frequent maintenances and inspections of the device.

SUMMARY OF THE INVENTION

In view of the above problems, it is a primary object of the present invention to provide a spectrophotometric method and apparatus capable of performing a transmission measurement of a sample solution with a small volume of about 1 to 2 μL or less in a simplified structure and in a user-friendly manner.

In order to achieved this object, according to a first aspect of the present invention, there is provided a spectrophotometric method comprising the steps of: providing a sampler including a flat plate member formed with a sample-holding hole which penetrates the flat plate member and has a sectional area simply decreasing in a thickness direction from a first surface to a second surface of the flat plate member; holding a target sample solution in the sample-holding hole of the sampler positioned approximately horizontally while orienting the first surface in an upward direction; emitting a measurement light to the held sample solution from above or below the flat plate member; and analyzing a transmitted light passing through the sample solution.

According to a second aspect of the present invention, there is provided A spectrophotometric apparatus comprising: a sample-solution holding sampler including a flat plate member formed with a sample-holding hole which penetrates the flat plate member and has a sectional area simply decreasing in a thickness direction from a first surface to a second surface of the flat plate member; sampler support means for supporting the sampler approximately horizontally while orienting the first surface in an upward direction; and a measurement optical system for emitting a measurement light into the sample-holding hole of the sampler supported by the sampler support means, from above or below the flat plate member, and receiving a light passing through the sample-holding hole. The measurement optical system is designed to analyze a target sample solution which is held in the sample-holding hole of the sampler supported approximately horizontally by the sampler support means.

In the above spectrophotometric method and apparatus of the present invention, a sample solution is dropped into the sample-holding hole of the sample positioned approximately horizontally while orienting the first surface in an upward direction. Further, the sample-holding hole has a sectional area gradually decreasing in a downward direction. Thus, the sample solution dropped and received in the sample-holding hole is hold in the sample-holding hole based on a surface tension of the droplet. That is, the sample-holding hole having upper and lower openings is filled with the sample solution. The measurement light is emitted to vertically penetrate the held sample solution, and then a transmitted light subject to optical absorption by the held sample solution is analyzed. The measurement optical system may have either one of a configuration designed to directly detect the measurement light as a monochromatic light and a configuration designed to disperse a multi-wavelength light (e.g. white light) selected as the measurement light, in a wavelength dependent manner or by wavelength, using a spectroscope, and then detect the resulting light with dispersed wavelength components.

As above, the above spectrophotometric method and apparatus of the present invention can analyze a sample solution with an extremely small volume of the order capable of being held in the sample-holding hole based on a surface tension. That is, a required volume of sample solution may be only about 1 to 2 µL or less. This shows suitability for analyses of a sample solution with a small volume, such as a biological sample. In addition, a sample solution can be set up only by dropping the sample solution into the sample-holding hole. Thus, operations for analysis can be performed in a drastically simplified manner without a time-consuming operation. Further, the sample solution has a contact with only the sample-holding hole and its surrounding of the sampler, and the sample-holding hole has the upper and lower openings. This makes it possible to readily perform a cleaning operation for completely removing the sample solution attached on the sampler. Furthermore, the sampler itself can be formed at an extremely low cost to reduce an analytic cost even if the sampler is used in a disposable manner. The sample solution has no contact with a body of the apparatus. Thus, the costly apparatus body can be kept from being damaged and contaminated so as to avoid an increase in burden of maintenance/inspection.

In the spectrophotometric method and apparatus of the present invention, the sampler may be formed in various shapes. In one preferred embodiment, the sample-holding hole of the sampler is formed in a truncated conical shape. While even a sample-holding hole formed, for example, in a truncated horn shape, can maintain the function of holding a sample solution based on a surface tension, corners residing inside the sample-holding hole are liable to cause residua of the sample solution therein. In contrast, the sample-holding hole having a truncated conical shape can eliminate such corners to facilitate a cleaning operation.

In the spectrophotometric method and apparatus of the present invention, if a volume of a sample solution to be dropped into the sample-holding hole of the sampler fluctuates, the fluctuation leads to variation in light path length which becomes an adverse factor causing deteriorations in analytic accuracy and reproducibility. Practically, it is difficult to perfectly drop the sample solution at a constant volume. Thus, it is preferable to further provide correction means for correcting a variation in light path length due to fluctuation in volume of a sample solution held in the sample-holding hole of the sampler.

As a specific example of the correction means, in the case where water is used as a solvent in the sample solution, the correction may be performed by monitoring an absorbed amount of near-infrared light subject to optical absorption by water, calculating a coefficient for correcting a variation in light path length, based on the monitored absorbed amount, and multiplying an intensity of received near-infrared light by the calculated coefficient. The correction means makes it possible to eliminate or reduce an error due to fluctuation in volume of a sample solution dropped into the sample-holding hole of the sampler so as to achieve enhanced analytic accuracy and reproducibility.

While a spectroscope may be fundamentally disposed before or after the held sample solution, as described above, the following point should be considered. In the present invention, the sample solution is extremely small in volume, and the sample-holding hole has the upper and lower openings. These factors are likely to cause vaporization of a solvent in the sample solution, and change in concentration of the sample in the held sample solution. Thus, it is desirable to complete a measurement within the shortest possible time after a sample solution is dropped into the sampler. In view of this need, if it is necessary to acquire an absorbance spectrum in a given wavelength range instead of a single wavelength, it is preferable that the measurement light to be emitted to the held sample solution consists of a multiple-wavelength light, and the measurement optical system is designed to spectrally disperse a transmitted light passing through the held sample solution, using a spectroscope, and detect the resulting light with dispersed wavelength components approximately simultaneously.

This configuration makes it possible to detect light having a given wavelength range approximately simultaneously without the need for sequentially scanning wavelengths of a monochromatic light picked up from a spectroscope as in a so-called sequential spectrophotometer. Thus, the measurement can be completed within a short time to avoid the risk of deterioration in accuracy due to the aforementioned vaporization of the solvent.

BRIEF DESCRIPTION OF THE DRAWINGS

FIGS. 4(a) and 4(b) are graphs showing test results on the level of variation in absorbance, wherein FIG. 4(a) is a test result obtained using no light-path-length correction, and FIG. 4(b) shows is a test result obtained using a light-path-length correction.

DESCRIPTION OF THE PREFERRED EMBODIMENTS

Figure 1:
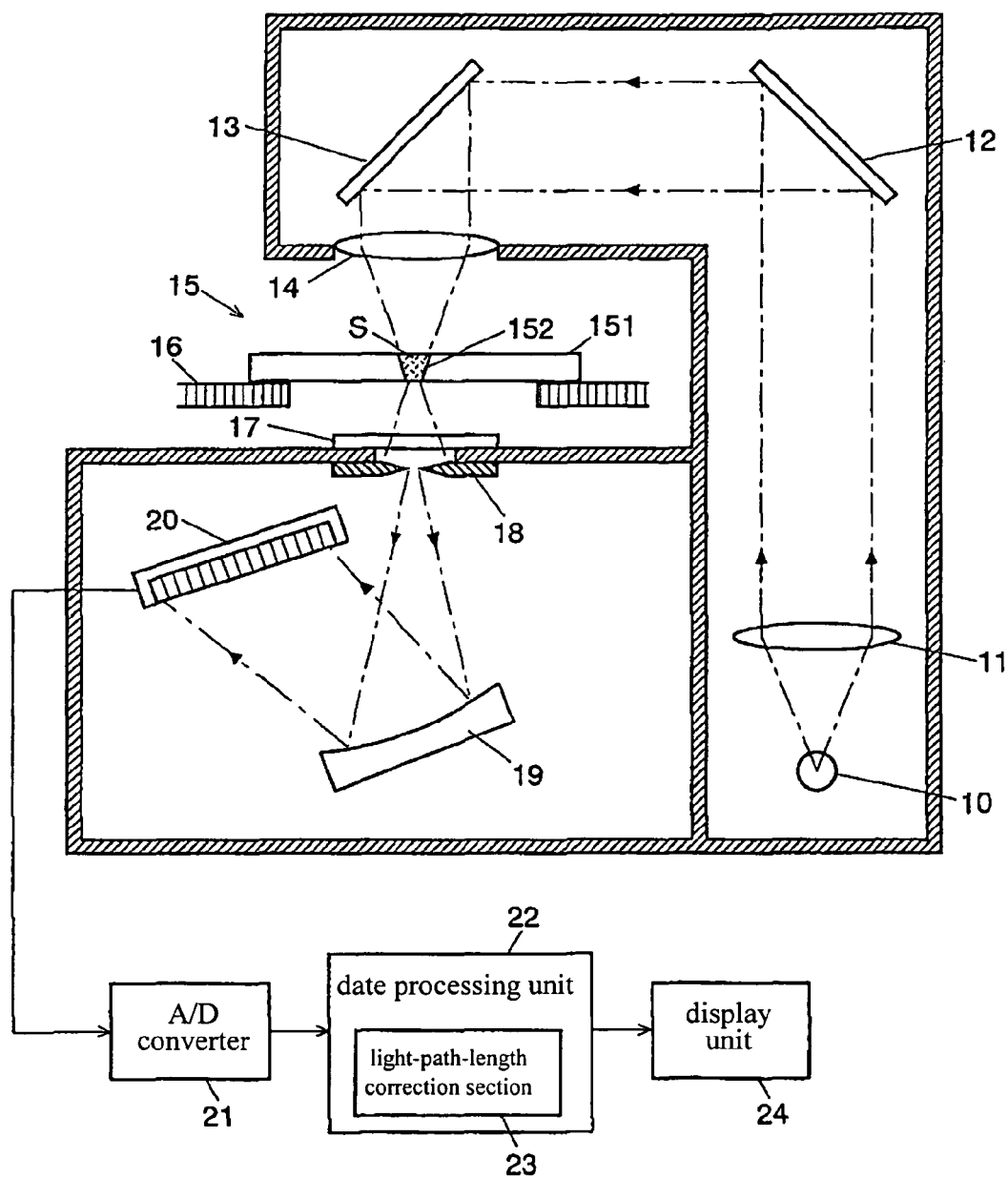
FIG. 1 is a schematic block diagram showing an ultraviolet-visible spectrophotometric apparatus according to one embodiment of the present invention.
Figure 2:
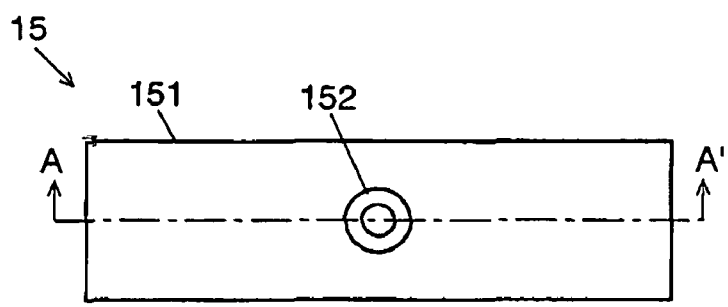
FIG. 2(a) is a top plan view showing a sampler for use with the ultraviolet-visible spectrophotometric apparatus in FIG. 1.
FIG. 2(b) is a sectional view taken along the line A-A' in FIG. 2(a).
Figure 2:
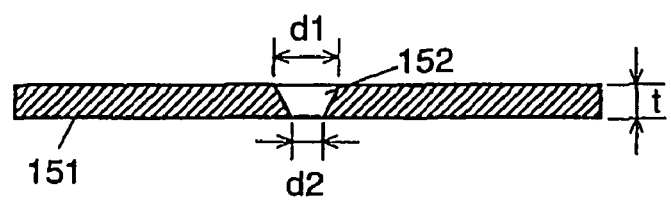
Figure 3:
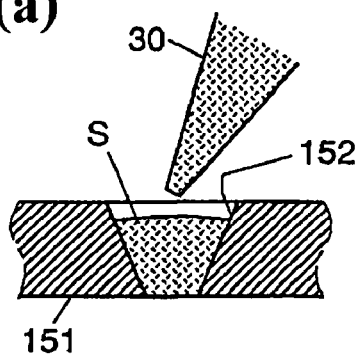
FIGS. 3(a) to 3(c) are explanatory schematic diagrams of an analytic procedure using the ultraviolet-visible spectrophotometric apparatus in FIG. 1.
Figure 3:
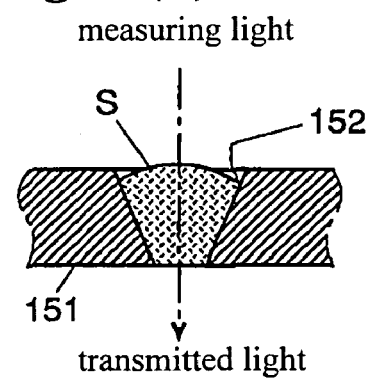
Figure 3:
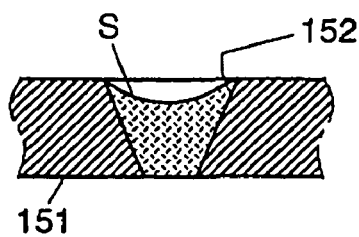

With reference to the drawings, an ultraviolet-visible spectrophotometric apparatus according to one embodiment of the present invention, which implements a spectrophotometric method according to one embodiment of the present invention, will now be described. FIG. 1 is a schematic block diagram showing the ultraviolet-visible spectrophotometric apparatus according to this embodiment. FIG. 2(a) is a top plan view showing a sampler 15 for use with the ultraviolet-visible spectrophotometric apparatus, and FIG. 2(b) is a sectional view taken along the line A-A' in FIG. 2(a). FIGS. 3(a) to 3(c) are explanatory schematic diagrams of an analytic procedure.

In FIG. 1, light emitted from a light source 10 is collimated into a parallel light by a lens 11, and them reflected by a reflecting mirror 12 and a reflecting mirror 13 in this order. Then, the reflected light is focused by a lens 14, and emitted as a measurement light to a sample to be analyzed, or a target sample, from approximately directly above the target sample. The target sample is a droplet S of a sample solution held by a sampler 15 which is supported by a sampler holder 16 in a space between the lens 14 and a window plate 17. The measurement light is subjected to optical absorption depending on components of the sample in the course of passing through the droplet S, and emitted downward as a transmitted light. The transmitted light passing through the transparent plate 17 is restricted in light band by a slit 18 and then introduced to a diffraction grating 19. The transmitted light is spectrally dispersed by the diffraction grating 19, and the resulting light with dispersed wavelength components is detected approximately simultaneously by a multichannel detector 20, such as a CCD linear sensor.

A detection signal from the detector 20 is converted into digital data through an A/D converter 21, and sent to a data processing unit 22. The data processing unit 22 is operable to calculate an absorbance by the droplet S, for example on a wavelength-by-wavelength basis, based on the digital data entered therein, so as to produce an absorbance spectrum in a given wavelength range, and display the absorbance spectrum on a screen of a display unit 24. Typically, the data processing unit 22 substantially comprises a general-purpose personal computer, and intended functions of the data processing unit 22 can be achieved by operating the personal computer according to a control/processing program. For achieving one of the functions, the data processing unit 22 includes a light-path-length correction section 23 as described in detail later.

As shown in FIGS. 2(a) and 2(b), the sampler 15 comprises a thin flat plate member 151 formed with a truncated cone-shaped sample-holding hole 152 which penetrates the flat plate member 151 in its thickness direction. Specifically, the sample-holding hole 152 has an upper opening in an upper surface of the sampler 15, and a lower opening in a lower surface of the sampler 15. The upper opening has a diameter d1 of 2 mm, and the lower opening has a diameter d2 of 1 mm. The flat plate member 151 has a thickness t of 1 mm. As shown in FIG. 2(a), the truncated cone-shaped sample-holding hole 152 has a sectional area simply decreasing in a direction from the upper surface (first surface) to the lower surface (second surface).

The sampler 15 serves as a means to hold a sample solution based on a surface tension. Preferably, the sampler 15 is formed in such a manner as to allow a droplet in the sample-holding hole 152 to have a rounded shape close to a spherical shape, for the after-mentioned reason. For this purpose, a contact surface of the ample-holding hole 152 with the sample solution preferably has a property of repelling a solvent in the sample solution. For example, the flat plate member 151 may be made of a synthetic resin having high water-repellency, such as ethylene tetrafluoride resin, or the contact surface may be subjected to a water-repellent treatment. Further, in order to prevent the measurement light from being transmitted through a portion of the sampler other than the sample-holding hole 152, the flat plate member 151 is preferably made of a material having no light transmittance, or preferably has a surface coated by a light-shielding material.

A procedure of an analysis using the ultraviolet-visible spectrophotometric apparatus according to this embodiment will be described below. As shown in FIG. 3(a), an analyst drops a given volume of sample solution into the sample-holding hole 152 of the sampler 15 supported approximately horizontally as shown in FIG. 1, using a micropipette 30 or the like. When the sampler 15 has the aforementioned dimensions, the sample solution dropped into the sample-holding hole 152 in a volume of about 1 µL can be sufficiently analyzed.

As shown in FIG. 3(b), the dropped sample solution is formed into a droplet having an approximately spherical shape and held in the sample-holding hole 152 while being kept from flowing out of the lower opening of the sample-holding hole 152 by a surface tension. If the sample-holding hole 152 in the flat plate member 151 of the sampler 15 has an inner surface having poor water-repellency (excellent hydrophilic property), water as a solvent in the sample solution will spread over the inner surface of the sample-holding hole 152 and thereby a spherical-shaped droplet cannot be obtained, as shown in FIG. 3(c). In this case, it is difficult to keep a light path length vertically along a light axis at a constant value. This variation in light path length becomes an adverse factor causing deterioration in analytic accuracy. This is the reason why the inner or contact surface of the sample-holding hole 152 in the flat plate member 151 of the sampler 15 preferably has enhanced water-repellency.

After the droplet S is set up in the flat plate member 151 of the sampler 15 in the above manner, the measurement light is emitted to the sample solution S from directly above the sample solution S in the downward direction, as described above. A light axis of the measurement light is set in such a manner as to be aligned with an axis of the sample-holding hole 152 as shown in FIG. 3(b), and therefore a transmitted light passing through the droplet S gets out of the lower opening of the sample-holding hole 152 vertically downward. That is, each of an inlet interface of the measurement light to the droplet S and an exit interface of the transmitted light is an interface between the sample solution and air (or vacuum atmosphere), but any member, such as glass, is not interposed therein.

The transmitted light subjected to optical absorption in the course of passing through the droplet S held in the sample-holding hole 152 is spectrally dispersed, and an absorbance spectrum is calculated based on an intensity of the light with dispersed wavelength components. As above, the ultraviolet-visible spectrophotometric apparatus according to this embodiment makes it possible to perform a spectral transmission measurement, such as absorbance or transmittance, of an extremely small volume of sample solution, in a simplified manner. In addition, the ultraviolet-visible spectrophotometric apparatus is designed to perform a simultaneous multi-wavelength detection using the multichannel detector 20. Thus, a spectrophotometry in a wide wavelength rangy can be completed within a short time. This makes it possible to substantially ignore an influence of vaporization of the solvent even if the droplet S to be analyzed is extremely small in volume.

Further, the sampler 15 is formed simply by perforating a flat plate, and readily detached from a body of the apparatus. Thus, a cleaning operation can be facilitated to prevent a cross-contamination. Furthermore, a cost of the sampler 15 itself can be reduced at a low value. Thus, even if the sampler 15 is used in a disposable manner, a significant financial burden will not be imposed on a user.

It is understood that the dropping of the sample solution to the sample-holding hole 152 may be automatically performed instead of the analyst's manual operation using the micropipette. in either case, as long as a sample-solution dropping device, such as a micropipette or an equivalent device, is used, it is difficult to drop a sample solution at a constant volume, and it should be expected that a volume of the droplet S generally fluctuates in the range of about ±10%. If a volume of the droplet S in the sample-holding hole 152 fluctuates, a light path length of the measurement light in the droplet S will vary, as seen in FIG. 3(b). If the light path length increases, an apparent concentration of the sample in the sample solution will increase, and the increase in apparent concentration will appear as variation in absorbance.

The light-path-length correction section 23 is provided as a means to correct a variation of the light wave length due to fluctuation in volume of the droplet. In this correction, a lamp having an emission spectrum in a near-infrared range as well as an ultraviolet-visible range, such as a xenon lamp, is used as the light source 10. It is understood that, an ultraviolet-visible lamp and a near-infrared lamp may be used in combination in such a manner as to allow lights from these lamps to be selectively emitted to the sample solution.

If a solvent in a target sample solution consists of water, the water absorbs a light component of a specific wavelength in the near-infrared range. The sample itself in the sample solution seldom or never absorbs the light of the specific wavelength. Thus, an absorbed amount of the light component of the specific wavelength becomes larger as a light path length in the droplet S increases. The light-path-length correction section 23 is operable to monitor an absorbed amount of the light component of the specific wavelength, and calculate a correction coefficient based on a ratio of the monitored absorbed amount to a predetermined reference value. For example, when an absorbed amount of the light component of the specific wavelength in a certain droplet S is A1, and a corresponding reference value is Aref, a correction coefficient K is defined by the following formula:

$$K=Aref/A1$$

If A1=Aref, the correction coefficient K will be 1. The correction coefficient K increases as A1 becomes larger and larger than Aref, i.e. the absorbed amount increases.

Figure 4:
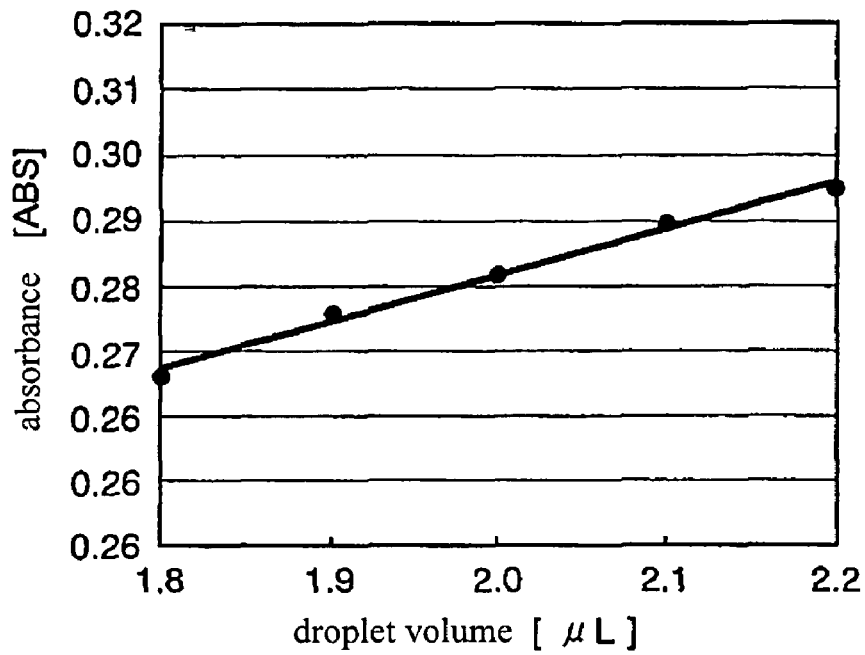
Figure 4:
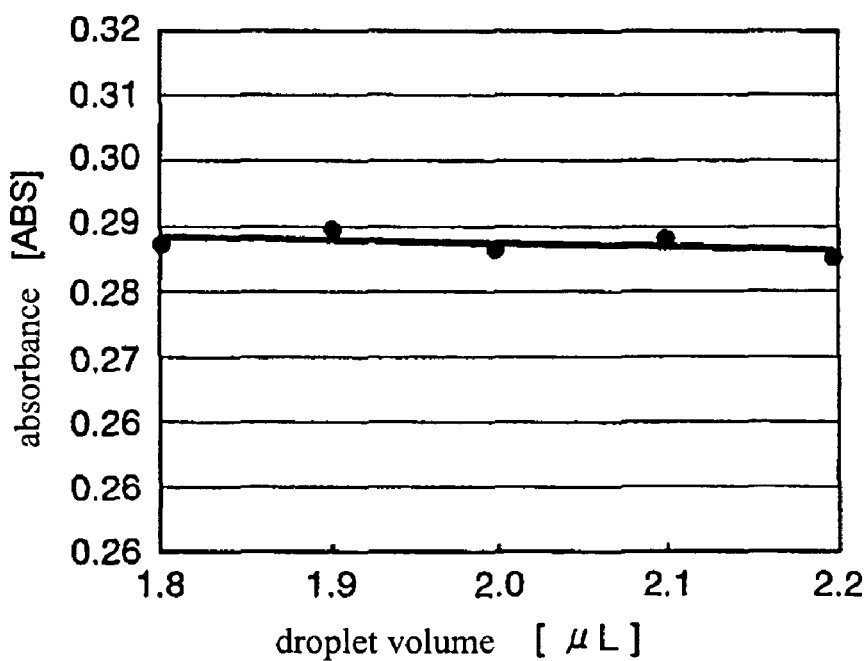

Then, an absorbed amount of the acquired ultraviolet-visible light is multiplied by the calculated correction coefficient K to correct the absorbed amount. When A1 is greater than Aref, a light path length is greater than a desirable value, and thereby an absorbed amount of the ultraviolet-visible light apparently becomes higher. Through the multiplication using the calculated correction coefficient K, the absorbed amount can be corrected to a smaller or adequate value. In this manner, an influence of fluctuation in volume of a sample solution to be dropped can be eliminated to achieve enhanced analytic accuracy and reproducibility. FIGS. 4(a) and 4(b) show test results on the level of variation in absorbance, wherein FIG. 4(a) is a test result obtained without using the light-path-length correction, and FIG. 4(b) shows is a test result obtained using the light-path-length correction. As seen in FIGS. 4(a) and 4(b), given that a fluctuation in 2 μL of the droplet is ±10%, the variation in absorbance is about 10% when the correction id not performed. In contrast, when the correction id not performed, the variation in absorbance is drastically reduced to 1% or less.

When the solvent consists of water, an absorption wavelength of water exists at about 980 nm, 1160 nm and 1470 nm. The aforementioned specific wavelength may be any one selected from these wavelengths. In a photodiode array (PDA) detector for used in ultraviolet-visible spectrophotometry, an upper limit of a detectable wavelength is typically about 1100 nm. Thus, when it is necessary to measure an absorbed amount by water using the PDA detector, 980 nm may be selected as the specific wavelength. In terms of absorption intensity, a maximum value appears at 1470 nm. Thus, the specific wavelength may be set at 1470 nm to obtained enhanced accuracy in calculation of the absorbed amount. In this case, it is required to provide a different type of spectrophotometric detector from the PDA detector.

Figure 5:
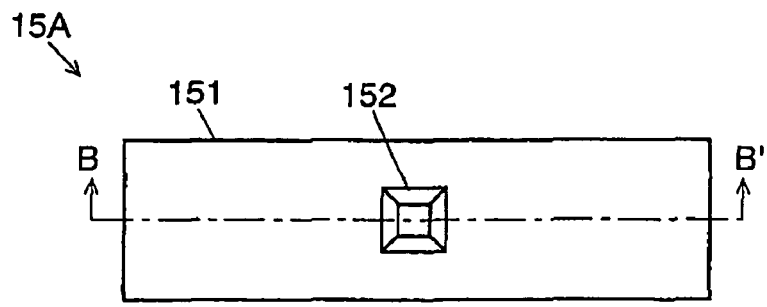
FIG. 5(a) is a top plan view showing one example of modification of the sampler.
FIG. 5(b) is a sectional view taken along the line B-B' in FIG. 5(a).
Figure 5:
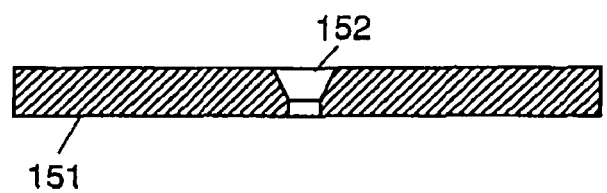

FIG. 5(a) is a top plan view showing one example of modification of the above sampler, and FIG. 5(b) is a sectional view taken along the line B-B' in FIG. 5(a). In this example, a sample-holding hole 152 has a truncated quadrangular cone-shaped upper portion, and a quadrangular prism-shaped lower portion continuing from a bottom edge of the upper portion. This sample-holding hole 152 having this configuration can also hold a sample solution therein in the form of a droplet. It is obvious to those skilled in the art that various configurations other than the above example may be conceivable.

One advantage of the spectrophotometric apparatus of the present invention is that a sample solution has a contact with only the sample-holding hole of the sampler 15 and the vicinity thereof. This allows a spectrophotometric apparatus to be designed to measure a plurality of sample solutions continuously and automatically. In such a continuous measurement for a plurality of sample solutions, a sampler (15B, 15C, 15D) having a plurality of sample-holding holes 152, as shown in FIGS. 6 to 8, may be used.

Figure 6:
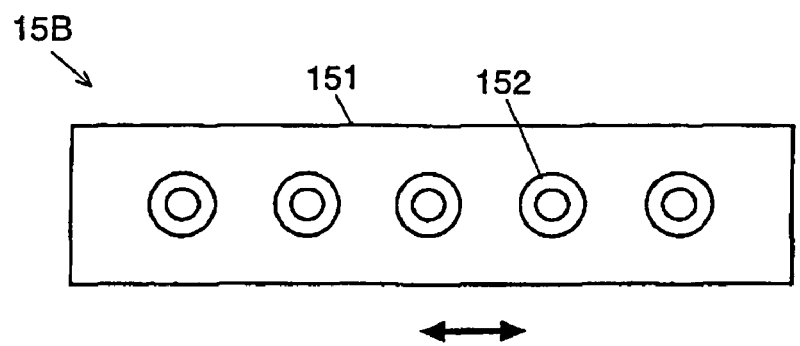
FIG. 6 is a top plan view showing one example of a sampler for use in a continuous measurement.

A sampler 15B illustrated in FIG. 6 comprised a rectangular-shaped flat plate member 151 penetratingly formed with a plurality (five in this example) of sample-holding holes 152 aligned in a line. A driving mechanism may be provided to linearly reciprocate the sampler 15B in directions as indicated by the arrows in FIG. 6 and move the sample-holding holes 152 one-by-one to a measurement-light emitting position, so as to perform the automatic/continuous measurement.

Figure 7:
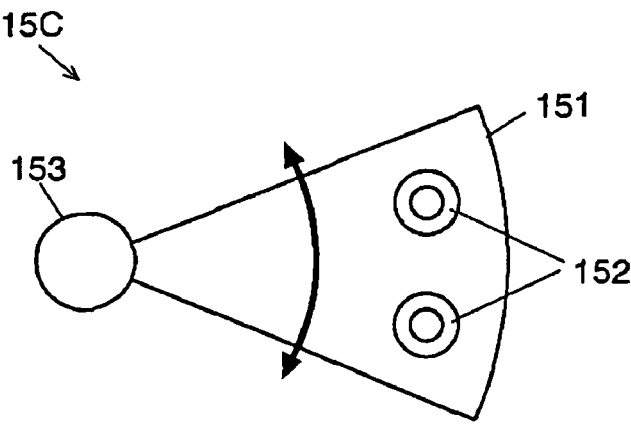
FIG. 7 is a top plan view showing another example of the sampler for use in the continuous measurement.

A sampler 15C illustrated in FIG. 7 comprises a sector-shaped flat plate member 151 penetratingly formed with a plurality (two in this example) of sample-holding holes 152 arranged along a circumference of a circle having a center defined by a shaft 153. A driving mechanism may be provided to rotate the sampler 15C in directions as indicated by the arrows in FIG. 7 and move the sample-holding holes 152 one-by-one to a measurement-light emitting position, so as to perform the automatic/continuous measurement.

Figure 8:
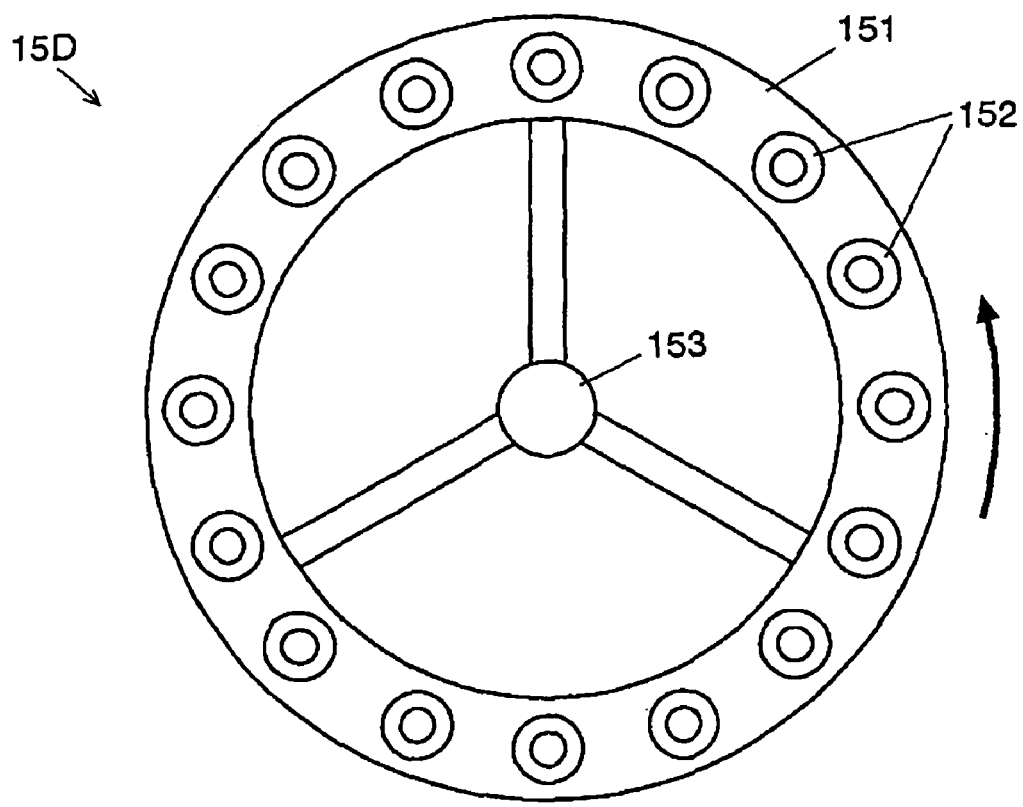
FIG. 8 is a top plan view showing yet another example of the sampler for use in the continuous measurement.
Figure 9:
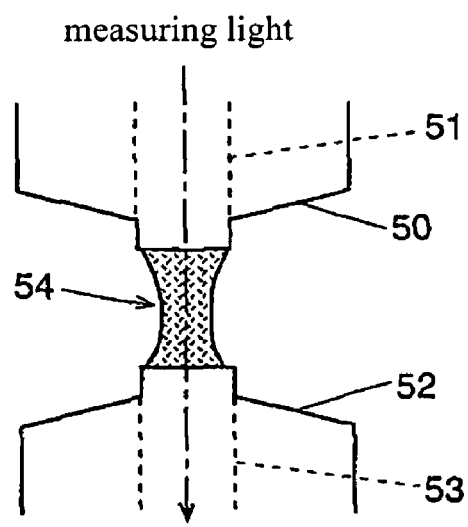
FIG. 9 is a fragmentary schematic diagram showing a conventional spectrophotometer for a small volume of sample solution.

A sampler 15D illustrated in FIG. 8 comprises an annulus ring-shaped flat plate member 151 penetratingly formed with a plurality (sixteen in this example) of sample-holding holes 152 arranged along a circumference of a circle having a center defined by a shaft 153. A driving mechanism may be provided to rotate the sampler 15D in a direction as indicated by the arrow in FIG. 8 and move the sample-holding holes 152 one-by-one to a measurement-light emitting position, so as to perform the automatic/continuous measurement.

In the above samplers for a continuous measurement, a marking indicative of each position of the sample-holding holes 152 may be formed on the flat plate member 151, and the sampler may be moved while automatically recognizing each position of the sample-holding holes 152 using a marking detection mechanism, such as an optical sensor, mounted on the body of the spectrophotometric apparatus.

When the number of the sample-holding holes 152 is two or several, a sample solution may be set up in all of the sample-holding holes 152 before initiation of the continuous measurement. In the case where the sampler has many sample-holding holes 152, if a sample solution is dropped into all of the sample-holding holes 152 before initiation of the continuous measurement, the aforementioned problem about vaporization of the solvent is likely to occur. Thus, it is preferable to operate a sampler driving mechanism in conjunction with an automatic sample-solution dropping device in such a manner that the sample solution is dropped into one of the sample-holding holes to be subjected to analysis next, while moving the sampler, and the sample-holding hole after completion of setup of the sample solution is moved to the measurement-light emitting position in a sequential manner, so as to minimize a time period between the dropping of the sample solution and the initiation of the measurement.

One embodiment of the present invention has been shown and described. It is obvious to those skilled in the art that various changes and modifications may be made therein without departing from the spirit and scope thereof as set forth in appended claims. For example, the configuration of the measurement optical system in the above embodiment may be appropriately modified. As one example, the measurement optical system may be designed to emit a measurement light upward from below the sample-holding hole of the sampler, and spectrophotometrically measure a transmitted light. Further, the sampler is not limited to the specific material and dimensions in the above embodiment.

What is claimed is:

1. A spectrophotometric method for a small volume of sample solution, comprising the steps of:
    providing a sampler including a flat plate member formed with at least one sample-holding hole which penetrates the flat plate member and has a sectional area simply decreasing in a thickness direction from a first surface to a second surface of the flat plate member;
    holding a target sample solution in said at least one sample-holding hole of said sampler positioned approximately horizontally while orienting said first surface in an upward direction and wherein said sample solution is held in said at least one sample-holding hole based on a surface tension of said sample solution, and said surface tension prevents said sample solution from flowing through said at least one sample-holding hole during analysis;
    emitting a measurement light to said held sample solution from above or below said flat plate member; and
    analyzing a transmitted light passing through said sample solution;
    wherein said step of analyzing includes correcting a variation in light path length due to fluctuation in volume of a sample solution held in said at least one sample-holding hole.

2. A spectrophotometric apparatus comprising:
    a sample-solution holding sampler including a flat plate member formed with at least one sample-holding hole which penetrates the flat plate member and has a sectional area simply decreasing in a thickness direction from a first surface to a second surface of the flat plate member;
    sampler support means for supporting said sampler approximately horizontally while orienting said first surface in an upward direction;
    a measurement optical system for emitting a measurement light into said at least one sample-holding hole of said sampler supported by said sampler support means, from above or below said flat plate member, and receiving a light passing through said at least one sample-holding hole, said measurement optical system being designed to analyze a target sample solution which is held in said at least one sample-holding hole of said sampler supported approximately horizontally by said sampler support means and wherein said sample solution is held in said at least one sample-holding hole based on a surface tension of said sample solution, and said surface tension prevents said sample solution from flowing through said at least one sample-holding hole during analysis; and
    correction means for correcting a variation in light path length due to fluctuation in volume of a sample solution held in said at least one sample-holding hole.

3. The spectrophotometric method as defined in claim 1, wherein said at least one sample-holding hole has a truncated conical shape.

4. The spectrophotometric method as defined in claim 1, wherein said measurement light consists of a multiple-wavelength light, wherein said step of analyzing includes spectrally dispersing the transmitted light, and detecting the resulting light with dispersed wavelength components approximately simultaneously.

5. The spectrophotometric apparatus as defined in claim 2, wherein said at least one sample-holding hole has a truncated conical shape.

6. The spectrophotometric apparatus as defined in claim 2, wherein said measurement light consists of a multiple-wavelength light, wherein said measurement optical system includes a spectroscope for spectrally dispersing a transmitted light passing through the sample solution, and means for detecting the resulting light with dispersed wavelength components approximately simultaneously.

7. The spectrophotometric method as defined in claim 1, wherein the first surface of the flat plate includes an upper opening and the second surface of the flat plate includes a lower opening, wherein the transmitted light passing through said sample solution passes through the upper opening and the lower opening.

8. The spectrophotometric apparatus as defined in claim 2, wherein the light passing through the at least one sample-holding hole passes through the target sample solution.

9. The spectrophotometric apparatus as defined in claim 8, wherein the first surface of the flat plate includes an upper opening and the second surface of the flat plate includes a lower opening, wherein the transmitted light passing through said sample solution passes through the upper opening and the lower opening.

10. The spectrophotometric method as defined in claim 1, wherein the at least one sample-holding hole is a plurality of sample-holding holes that are fluidly segregated from each other.

11. The spectrophotometric method as defined in claim 1, wherein the sample solution is a droplet.

12. The spectrophotometric apparatus as defined in claim 2, wherein the at least one sample-holding hole is a plurality of sample-holding holes that are fluidly segregated from each other.

13. The spectrophotometric apparatus as defined in claim 2, wherein the sample solution is a droplet.

14. The spectrophotometric method as defined in claim 1, wherein the sample solution is about 1 μL.

15. The spectrophotometric apparatus as defined in claim 2, wherein the sample solution is about 1 μL.

* * * * *